United States Patent [19]

Forman

[11] Patent Number: 5,267,959
[45] Date of Patent: Dec. 7, 1993

[54] LASER BONDING OF ANGIOPLASTY BALLOON CATHETERS

[75] Inventor: Michael R. Forman, St. Paul, Minn.

[73] Assignee: Schneider, Inc., Plymouth, Minn.

[21] Appl. No.: 800,201

[22] Filed: Nov. 29, 1991

[51] Int. Cl.$^5$ .................................. A61M 29/00
[52] U.S. Cl. .................................. 604/103; 606/194
[58] Field of Search ............... 604/96, 99, 101, 103; 606/192, 194

[56] References Cited

U.S. PATENT DOCUMENTS

| | | |
|---|---|---|
| 3,528,869 | 9/1970 | Dereniuk . |
| 3,769,117 | 10/1973 | Bowen et al. . |
| 3,953,706 | 4/1976 | Harris et al. . |
| 4,069,080 | 1/1978 | Osborne . |
| 4,251,305 | 2/1981 | Becker et al. . |
| 4,276,874 | 7/1981 | Wolvek et al. ............... 604/96 |
| 4,550,238 | 10/1985 | Van Herle et al. . |
| 4,733,047 | 3/1988 | Cruikshank et al. . |
| 4,777,951 | 10/1988 | Cribier et al. ............... 604/96 |
| 4,941,877 | 7/1990 | Montano, Jr. ............... 604/96 |
| 4,950,239 | 8/1990 | Gahara et al. ............... 604/96 |
| 4,958,634 | 9/1990 | Jang ............... 604/96 |
| 5,108,415 | 4/1992 | Pirchuk et al. ............... 606/194 |

FOREIGN PATENT DOCUMENTS

| | | |
|---|---|---|
| 0087403 | 8/1983 | European Pat. Off. . |
| 0131918 | 1/1985 | European Pat. Off. . |
| 1479239 | 6/1989 | Fed. Rep. of Germany . |
| 58-166168 | 3/1982 | Japan . |
| 61-103688 | 5/1986 | Japan . |

Primary Examiner—John D. Yasko
Assistant Examiner—Anthony Gutowski

[57] ABSTRACT

A balloon catheter which is assembled by a process of selectively concentrating laser energy along an annular fusion bond site at contiguous surface portions of a length of catheter tubing and a shaft or neck portion of a dilatation balloon. The laser energy wavelength, and the polymeric materials of the balloon and catheter, are matched for high absorption of the laser energy to minimize conductive heat transfer in axial directions away from the bond site. This minimizes crystallization and stiffening in regions near the bond site, permitting fusion bonds to be located close to the proximal and distal cones of the dilatation balloon while preserving the soft, pliant quality of the cones.

16 Claims, 4 Drawing Sheets

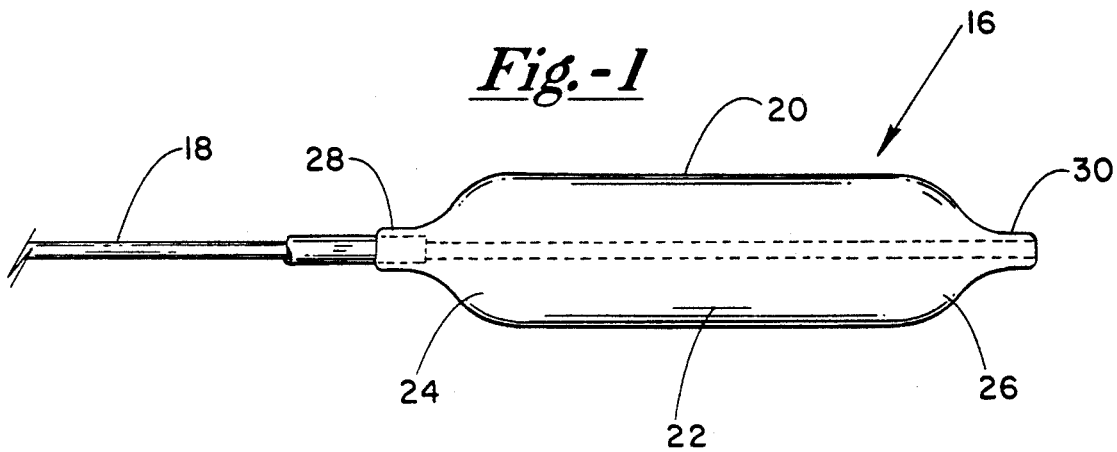
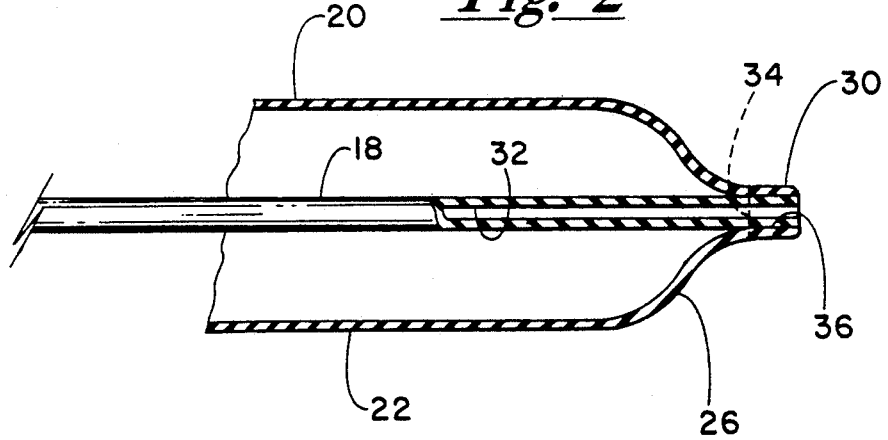

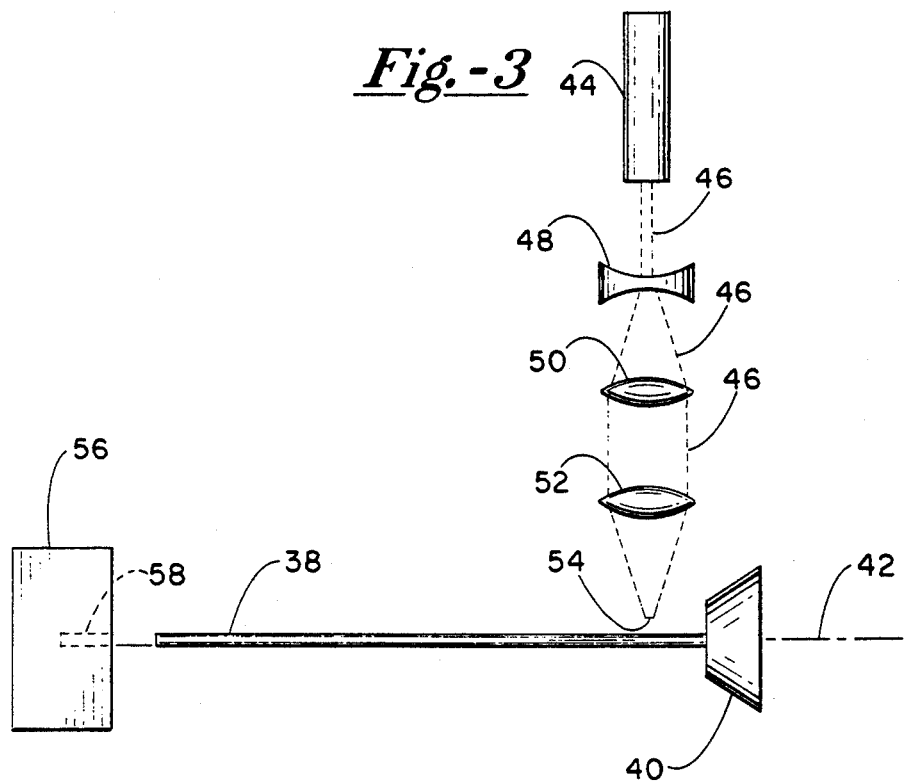
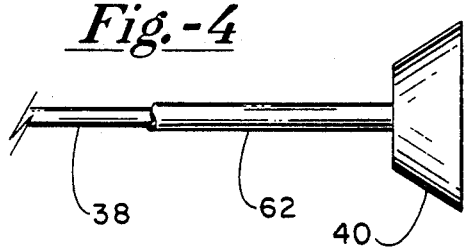
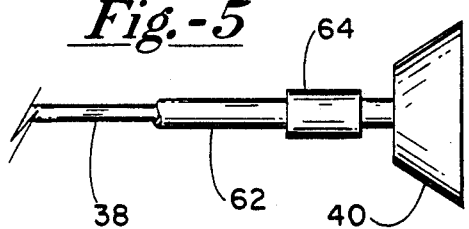
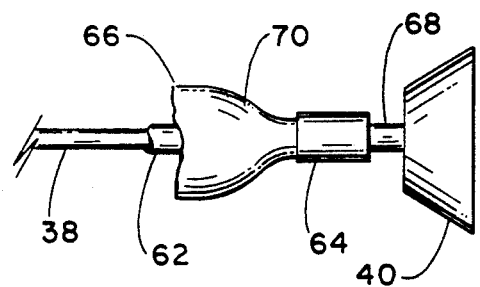

LASER BONDING OF ANGIOPLASTY BALLOON CATHETERS

BACKGROUND OF THE INVENTION

The present invention relates to dilatation balloon catheters employed in percutaneous transluminal angioplasty (PTA) and percutaneous transluminal coronary angioplasty (PTCA) procedures, and more particularly to the means for forming fluid tight seals between these catheters and their associated dilatation balloons.

Balloon catheters are well known for their utility in treating certain types of obstructions or occlusions in blood vessels, such as plaque build up. Angioplasty catheterization typically involves aligning a balloon catheter within the vessel to position its dilatation balloon at or along the obstruction. Then, fluid under pressure is supplied to the balloon through a balloon inflation lumen in the catheter, expanding the balloon against the obstruction.

In the manufacture of balloon catheters, it is essential that the bonds between the catheter and the surrounding dilatation balloon material be consistent, fluid tight and of sufficient strength to withstand the fluid pressures involved in balloon dilatation. Typically the dilatation balloon is mounted along the distal end region of the catheter and surrounds the catheter. A main body portion or medial region of the balloon has a diameter substantially larger than that of the catheter, with proximal and distal shafts or neck regions of the balloon having inner diameters substantially equal to the outer diameter of the catheter. Proximal and distal tapered portions, or cones, join the medial region to the proximal and distal shafts, respectively, with each cone diverging in the direction toward the medial region. The bonds between the balloon and catheter are formed along the proximal and distal shafts.

One known bonding approach for heat fusible materials involves the resistance heating of copper jaws, while the jaws press the respective balloon shafts onto and against the catheter. One result of the deformation of the balloon and catheter material is the formation of small, random channels at the balloon/catheter interface, giving rise to variations in the strength of different bonds. To compensate for this variance, bonds are given a sufficient length to provide the requisite burst strength, typically axial dimensions in the range of about 0.070–0.150 inches. The copper jaws heat the balloon shafts and catheter primarily by conduction but also by radiation. The heat causes crystallization and stiffening of the balloon and catheter material, not only at the bond site, but also in both directions axially of the bond, due to heat conduction through the balloon and the catheter, and heat radiation from the jaws.

Several disadvantages arise from crystallization and stiffening at and around the bond. Stiffness along the catheter distal tip, distal balloon shaft and proximal bond area interferes with movement of the catheter along narrow and convoluted arteries, and increase the risk of trauma to the intima. To the extent that crystallization extends to the balloon tapered cones, catheter maneuverability is further reduced, and cone stiffness prevents a complete evacuation of radiopaque dye or other fluid from the balloon following dilatation.

Crystallization at the cones can be reduced or avoided by sufficient axial spacing between each of the balloon cones and its associated bond. However, this approach further increases the minimum required length of the distal balloon shaft. More particularly, it has been found that a gap of at least 0.030 inches between the bond and balloon cone is required, to satisfactorily reduce crystallization in the cone.

Other approaches to bonding avoid the use of copper jaws. For example, U.S. Pat. No. 4,251,305 (Becker et al) discloses a non-contact method for heat sealing a balloon onto a catheter. A length of thin tubing is slid over an elongated shaft of the catheter. Shrink tubing is installed over the thin walled tubing at its ends, and overlapping the shaft, and partially shrunk. Then, lamps provide further radiant energy to form gradually tapering thermoplastic joints that bond the tubing and shaft. The device employed for bonding utilizes three lamps that emit energy along the visible and infrared spectra. Each lamp is situated near an elliptical reflector, at one of the foci of the ellipse. The bond or treatment area is near the other focus. While this approach avoids the problems arising from mechanical squeezing from the copper jaws, the undesirable axial conductive heat transfer remains a problem.

Adhesives can be employed as an alternative to fusion bonding. However, the adhesive layers add to the thickness of the catheter and increase its rigidity at the region of the bonds. Moreover, adhesive bonds are known to be generally inferior to fusion bonds.

Therefore, it is an object of the present invention to provide a process for forming balloon catheters with fusion bonds, with minimal heat conduction away from the bond sites.

Another object of the invention is to bond dilatation balloons to catheters in a manner to reduce thermal shock to the balloon cones, resulting in softer, more flexible dilatation balloons.

A further object is to provide balloon catheters with proximal and distal fusion bonds that are narrow, yet able to withstand high burst pressures.

Yet another object is to provide a balloon catheter more maneuverable along arteries and at reduced risk of trauma to the arteries.

SUMMARY OF THE INVENTION

To achieve these and other objects, there is provided a balloon catheter including an elongate pliable length of catheter tubing formed of a polymeric material and having a proximal end and a distal end. The balloon catheter further includes a polymeric dilatation balloon mounted to the catheter tubing near the distal end and in surrounding relation to the catheter tubing. The balloon includes a medial region, and proximal and distal shaft regions. Each shaft region is substantially smaller in diameter than the medial region. The balloon further includes proximal and distal tapered regions between the medial region and the proximal and distal neck regions, respectively. Each tapered region diverges in the direction from its associated shaft region to the medial region. Annular proximal and distal fluid tight fusion bonds are formed between the catheter tubing and the proximal and distal shaft regions, respectively. Each of the proximal and distal fusion bonds is within 0.030 inches of its associated one of the proximal and distal tapered regions. Moreover, each of the distal tapered regions is substantially free of crystallization.

Preferably the axial dimension of the distal fusion bond is at most 0.030 inches, and is less than 0.030 inches from the distal tapered region. This facilitates construction of a balloon catheter having a distal tip length of less than 0.06 inches, and more preferably less than 0.03 inches.

The shorter distal tip, in combination with the virtual absence of crystallization or stiffening of the adjacent balloon tapered region, results in substantially improved catheter maneuverability through convoluted vessels, during catheter insertion and also during catheter withdrawal. The catheter may be inserted into and used in vessels heretofore deemed inaccessible, and at substantially less risk of injury to the intima.

The reduced length distal tip is achieved while maintaining the integrity of the bond, due to a unique process for forming a fluid tight seal between a polymeric body and a polymeric dilatation member surrounding the body. The process includes the following steps:

a. positioning a dilatation member of polymeric material along and in surrounding relation to a body of polymeric material, with the dilatation member and body aligned to place a first surface portion of the dilatation member and a second surface portion of the body in a contiguous and confronting relation;

b. generating substantially monochromatic energy at a wavelength selected to at least approximately match a wavelength of maximum spectral absorption of the polymeric materials forming the dilatation member and body;

c. controllably directing the monochromatic energy into the body and the dilatation member to concentrate the amount of chromatic energy in a narrow bond site circumscribing the body and running along the interface of the first and second surface portions, thus to melt the polymeric materials along the bond site and the immediate region of the bond site; and d. allowing the previously melted polymeric material to cool and solidify to form a fusion bond between the body and dilatation member.

A preferred process employs a round body and an annular dilatation member, whereby the interface of the first and second surfaces is annular. A beam of the monochromatic energy is focused, with the focal area of the beam substantially at the interface. Then, the focal area is moved in a annular path along the interface, relative to the body and the dilatation member. This is readily accomplished by mounting the body and dilatation member substantially concentrically on an axis, and rotating the body and dilatation member about the axis while maintaining the beam stationary. Alternatively, the body and dilatation member are maintained stationary, while optomechanical means are employed to rotate the beam about the axis.

The preferred monochromatic energy is laser energy having a wavelength in the far infrared range, most preferably about 10.6 micrometers. Preferred polymeric materials, e.g. Hytrel, (polyester) for the catheter tubing and polyethylene terephthalate for the balloon, are highly absorptive of energy at this wavelength. The high absorption prevents any substantial conduction of heat from the bond site in either direction axially of the catheter. This reduces the energy required to form the fusion bond, and prevents any substantial crystallization and hardening of material in either direction from the bond site.

A $CO_2$ laser is used to provide a radiant energy beam at the preferred wavelength, and preferably operated in the $tem_{00}$ mode. In this mode, the focal area of the beam has a Gaussian distribution, further enhancing the concentration of heat at the bond site.

Thus, in accordance with the present invention, consistent and reliable fusion bonds are formed between catheters and dilatation balloons. The bonds are narrow in axial dimension, with relatively slight thermal shock and stiffening to the material near the bond site, in particular the cones or tapered regions of the dilatation balloon. The result is a balloon catheter that is more maneuverable, more pliable for a more complete evacuation of radiopaque dye, and more able to withstand high burst pressures.

IN THE DRAWINGS

For a further understanding of the above and other features and advantages, reference is made to the following detailed description and to the drawings, in which:

FIG. 1 is a side elevational view of the distal region of a balloon catheter constructed in accordance with the present invention;

FIG. 2 is an enlarged sectional elevational of a portion of FIG. 1;

FIG. 3 is a schematic view of tooling employed in the manufacture of the balloon catheter;

FIGS. 4-9 are schematic illustrations of various steps in the catheter assembly process;

DETAILED DESCRIPTION OF THE PREFERRED EMBODIMENTS

Figure 7:
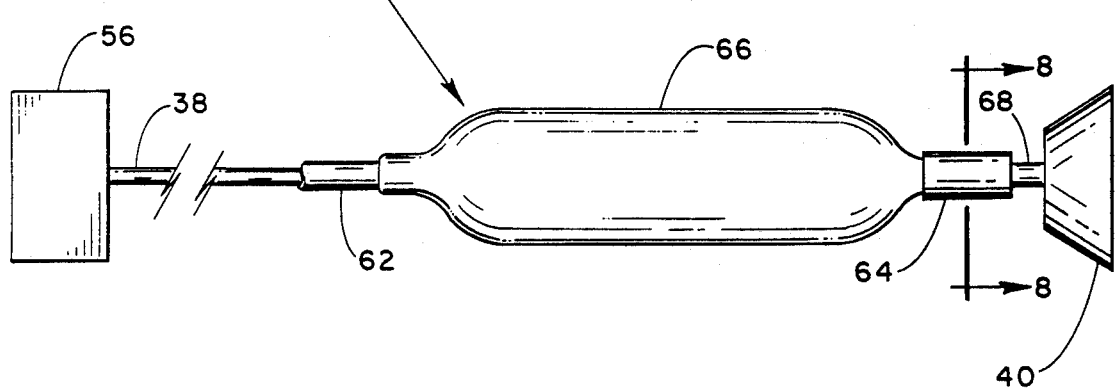

Turning now to the drawings, there is shown in FIG. 1 a balloon catheter 16, more particularly its distal end region. The balloon catheter includes an elongate and pliable length of catheter tubing 18 constructed of a body compatible polymeric material, preferably a polyester such as that sold under the brand name Hytrel. Other suitable materials include polyolefins, polyamides and thermoplastic polyurethanes, and copolymers of these materials. A dilatation balloon 20 surrounds catheter tubing 18 along the distal end region. The dilatation balloon is shown in its fully expanded or dilated configuration, as when the balloon contains a fluid, supplied under pressure to the balloon interior through a balloon inflation lumen (not shown) open to the proximal end of catheter tubing 18 and to the balloon interior.

When fully expanded, dilatation balloon 20 includes a main body or medial region 22, essentially an axially extended cylinder substantially concentric about the catheter tubing, and with a diameter substantially larger than that of the tubing, for example 0.060–0.13 inches as compared to an outside diameter in the range of 0.040–0.055 inches for catheter tubing 18. The appropriate balloon and catheter tubing diameters vary, depending upon factors such as the size of the vessel or other body cavity, and the procedure involved. At opposite ends of the medial region are a proximal tapered region or cone 24, and a distal tapered region or cone 26. The proximal cone converges in the direction away from the medial region toward an annular proximal neck region or shaft 28. The inner diameter of shaft 28 is substantially equal to the outer diameter of catheter tubing 18 in the region of the shaft, to provide an annular interface region along which the interior surface of shaft 28 and the exterior surface of tubing 18 confront one another and are contiguous.

Similarly, distal cone 26 converges in the distal direction from medial region 22 to a distal neck region or shaft 30. The distal shaft has an inner diameter substantially equal to the outer diameter of catheter tubing 18 in the region of the distal shaft. Consequently, the diameter of distal shaft 30 typically is less than the inner diameter of proximal shaft 28, because the catheter tubing is narrower along the distal shaft, e.g. due to the termination of the balloon inflation lumen proximally of shaft 30.

Dilatation balloon 20 preferably is constructed of a polymeric material that is sufficiently pliable or formable to readily achieve the enlarged configuration, yet is relatively inexpansible, i.e. tending to maintain the configuration shown in FIG. 1 under increased fluid pressure within the balloon. Polyethylene terephthalate (PET) is a preferred material for dilatation balloon 20. Among other suitable materials are nylon, polyolefin and their copolymers.

As seen in FIG. 2, catheter tubing 18 has a central lumen 32 to accommodate a guide wire (not shown) and, if desired, to provide a path for supplying drugs from the proximal end of the catheter tubing to a treatment site. A broken line at 34 indicates the proximal boundary of a fusion bond 36 between catheter tubing 18 and distal shaft 30. Fusion bond 36 is annular, and is located along the interface between the distal shaft and the catheter tubing. More particularly, the polymeric material along the inside surface of shaft 30 and the polymeric material along the exterior surface of tubing 18 become fused and form the bond as they cool and solidify, to provide a fluid tight seal between the catheter tubing and the dilatation balloon.

Preferably, bond 36 has an axial dimension of at most 0.030 inches, and is within 0.030 inches of distal cone 26, for a length of the catheter distal tip (including distal shaft 30 and the distal end of catheter tubing 18) of at most 0.060 inches. More preferably, the axial dimension of the bond is about 0.020 inches, and the bond is within 0.010 inches of cone 26. Further, the distal cone is substantially free of the crystallization that results from thermal shock from the heat of bond formation. One sign of crystallization is tactile, namely a hardness or stiffness in the cones when crystallized. A related indication can be observed in connection with tracking fixtures for testing the ability of a catheter to negotiate serpentine channels formed in the fixtures. Also, crystallized cones, as compared to cones free of crystallization, have a substantially more pronounced tendency to warp or form asymmetrically. Crystallization imparts an undesirable stiffness to the polymeric material, increasing the difficulty in maneuvering the balloon catheter through convoluted arteries. Such stiffness in the balloon also interferes with a complete evacuation of radiopaque dye or other fluid from the balloon following dilatation. An incompletely evacuated dilatation balloon is more difficult to withdraw after an angioplasty procedure. Thus, freedom from crystallization and stiffness, and a shorter distal tip, provide substantially improved catheter maneuverability.

By comparison, balloon catheters manufactured according to the conventional approach with heated copper jaws, require distal tips in which the bond, alone, has an axial length of at least 0.070 inches, and further must be spaced apart from the distal cone at least 0.030 inches due to the undesirable crystallization and stiffening of the balloon. In fact, the heated jaws cause substantial crystallization in the distal cone, in spite of the 0.030 inch spacing.

In accordance with the present invention, fusion bonds between the catheter tubing and dilatation balloon are formed by a noncontact process, resulting in bonds that are much narrower yet withstand burst pressure to the same degree as conventional bonds. Moreover, as compared to conventionally formed bonds, bonds formed according to the present invention can be positioned substantially closer to the cones of the dilatation balloon, without the crystallization or attendant stiffening.

Apparatus employed in forming the balloon catheter is illustrated diagrammatically in FIG. 3. The apparatus includes an elongate mandril 38 formed of stainless steel. The outside diameter of mandril 38 is approximately equal to the diameter of central lumen 32, so that the mandril receives catheter tubing 18 in sliding or slip fit fashion. The mandril is removably clamped within a jig or chuck 40, rotatable to rotate the mandril about a horizontal axis 42.

A system for directing monochromatic energy onto the mandril includes a laser source 44 generating a laser beam 46 with a wavelength in the far infrared range. Preferably the laser is a $CO_2$ laser, in which case the wavelength of beam 46 is about 10.6 microns. The beam is directed through a concave-concave lens 48 which expands the beam, and then to a convex-convex lens 50 which collimates the beam. The collimated beam is directed through a convex-convex lens 52, which focuses the beam at a focal point or area 54 slightly radially outwardly of the mandril exterior surface.

Near the free end of mandril 38 is a mandril guide 56 having an opening 58 slightly larger in diameter than the mandril. Guide 56 is movable axially of the mandril, between the location illustrated in which it is completely removed from mandril 38, and a support position in which the free end of the mandril is captured within opening 58, thus to stabilize the mandril rotation.

The assembly of a balloon catheter 60 begins with the placement of a length of catheter tubing 62 onto the mandril, whereupon the catheter tubing is slid along the mandril to the right as viewed in FIG. 3, until the distal end of the catheter tubing abuts jig 40 as shown in FIG. 4. Next, a relatively short 0.030 inches) length of heat shrink tubing 64, preferably constructed of a polyolefin, is positioned at least near the jig, surrounding the catheter tubing as shown in FIG. 5. Then, a dilatation balloon 66 is fit onto and about the catheter tubing, and moved slidably until a distal shaft 68 abuts jig 40. This involves inserting the distal shaft within heat shrink tubing 64 as shown in FIG. 6. Finally, mandril guide 56 is moved rightwardly as viewed in these figures, until mandril 38 is captured within opening 58. As seen from FIG. 7, heat shrink tubing 64 surrounds distal shaft 68, with a proximal portion of the heat shrink tubing overlapping the distal end region of a distal cone 70. If desired, heat shrink tubing 64 can be of a sufficient length to abut jig 40 when in the position shown.

Of primary importance, however, is a proper alignment of dilatation balloon 66 for bonding. Preferably, laser source 44 and the accompanying optics are movable axially of the mandril relative to jig 40, to selectively align the laser system with respect to the jig. For example, given an intended fusion bond width of 0.030 inches and an axial distance of 0.010 inches between the distal cone and the bond site, the laser system is positioned relative to the jig such that beam 46 is aligned on the intended center of the bond relative to the distal cone, i.e. at 0.025 inches from the cone.

Figure 8:
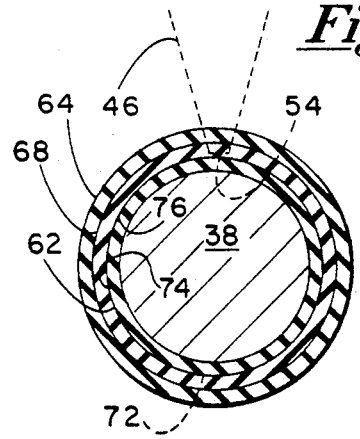

With the catheter tubing, dilatation balloon and heat shrink tubing properly positioned and with the laser system properly aligned, laser source 44 is fired to generate beam 46 while mandril 38 is rotated. Lens 52 focuses beam 46 to position focal area 54 as illustrated in FIG. 8, i.e. at the interface of catheter tubing 62 and distal shaft 68 of the dilatation balloon. Accordingly, the laser energy is concentrated along an annular bond site 72, defined by the rotation of the mandril, catheter tubing and balloon shaft relative to beam 46.

Several factors facilitate concentration of the laser energy resulting in effective bonds at relatively low wattage for laser source 44 and a relatively short duration for laser bonding. Of course, the focusing concentrates the energy of beam 46. Laser source 44 preferably is operated in the $tem_{00}$ mode, which results in a focal area having a Gaussian energy distribution, with maximum energy at the center of the focal area. Further, the wavelength of the laser energy and the polymeric materials of dilatation balloon 66 and catheter tubing 62 are matched, in the sense that both the PET and the Hytrel polyester have a high absorptivity for energy at the selected wavelength of 10.6 microns.

In practice, "matching" involves consideration of the cost and availability of laser sources as well as the polymeric materials of the catheter tubing and the dilatation balloon. Information on the absorptivity of various materials, with respect to wavelength of the energy, is available, for example in *The Infrared Spectra Atlas of Monomers and Polymers*, published by Sadtler Research Laboratories. In general, polymeric materials do not absorb energy uniformly, but rather exhibit bands of markedly increased absorptivity. For example, both polyethylene and polypropylene exhibit high absorptivity of energy at about 3.4 microns in wavelength, due to the $CH_2$ groups in these polymers. As polymers become more complex, so do their energy absorption spectra. Polyesters exhibit a band of absorption ranging from about 7-11 microns, a range that encompasses the 10.6 micron wavelength of laser beam 46. The tendency in polymers to exhibit wavelength-selective absorption is observed not only in connection with infrared energy, but throughout the electromagnetic spectrum.

As a result of these factors, heat sufficient to fuse an outer surface 74 of catheter tubing 62 and an inner surface 76 of distal shaft 68 is generated at a laser power of less than 10 watts, more particularly in the range of 3-4 watts. Mandril 38 is rotated at about 400 rpm during bonding, which tends to evenly distribute the heat about the bond site. A duration of from about 0.5 seconds to about 3 seconds of laser energy application has been found satisfactory for forming bonds that can withstand burst pressures exceeding 400 pounds per square inch, and the degree of control over the laser yields a high degree of consistency among the bonds. After the fused material cools and solidifies, heat shrink tubing 64 is removed.

A further benefit arises from the absorptivity match of the laser wavelength and polymeric materials of the catheter tubing and dilatation balloon. Due to the high absorptivity of these polymeric materials at the chosen wavelength, there is virtually no substantial conduction of heat in either axial direction away from the bond site. Portions of the tubing and balloon near the bond are not subject to undue heating that leads to crystallization and stiffening of the polymeric materials. Thus, a distal bond can be positioned within 0.010 inches of distal cone 70 without any substantial crystallization or stiffening of the cone. As noted above, bonding with heated copper jaws requires a spacing of at least 0.030 inches between the bond and the distal cone due to crystallization and stiffening. As a result, catheter balloons assembled according to the above described process can have substantially shorter distal tips and softer distal cones, for enhanced maneuverability in narrow, convoluted arteries.

Figure 9:
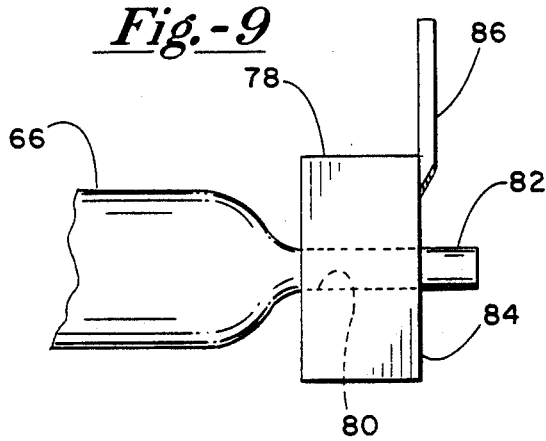

FIG. 9 illustrates a further step in the process, in which the distal bond is formed with an axial dimension larger than intended for the finished catheter, but with a controlled spacing from the distal cone. In this event, the steps discussed above are repeated without any substantial change. Then, the completed balloon catheter is inserted by its distal tip into a cutting fixture 78 (FIG. 9) with the distal tip contained in an opening 80 through the fixture. With distal cone 70 abutting the fixture as illustrated, an excess length portion 82 of the distal tip extends beyond an end wall 84 of the fixture, and is conveniently cut away from the remainder of the catheter with a blade 86 movable along the end wall.

Figure 10:
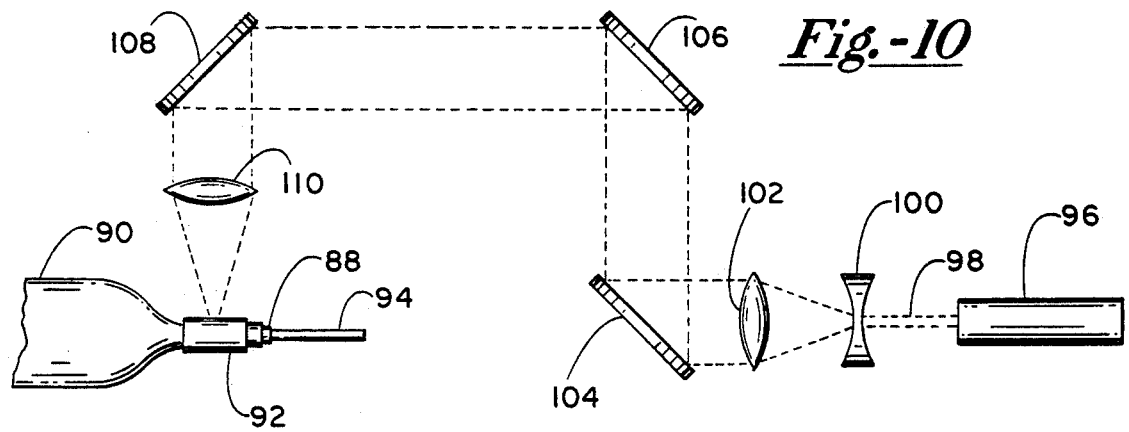
FIG. 10 is a schematic view of an alternative embodiment approach to manufacturing the balloon catheter.

FIG. 10 illustrates an alternative means for concentrating the laser energy at an annular bond site. A length of catheter tubing 88, a dilatation balloon 90 and heat shrink tubing 92 are supported on an elongate stationary pin 94. A laser source 96, also stationary, generates a beam 98 of the preferred wavelength of 10.6 microns. Beam 98 is directed through a concave-concave diverging lens 100, and then through a convex-convex lens 102 to collimate the beam. The collimated beam is diverted by a series of planar reflectors at 104, 106 and 108, and finally through a convex-convex focusing lens 110, which locates the beam at the interface between catheter tubing 88 and dilatation balloon 90.

With the tubing and balloon stationary, the required relative movement is achieved by rotating beam 98. More particularly, planar reflectors 104, 106 and 108 and lens 110 are mounted integrally with respect to each other, but rotatable relative to pin 94.

Figure 11:
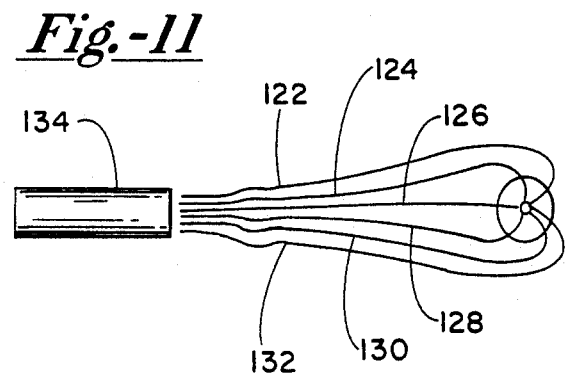
FIG. 11 is a schematic view of a laser generator and an array of optical fibers for supplying laser energy to the fixture according to a further embodiment approach.
Figure 12:
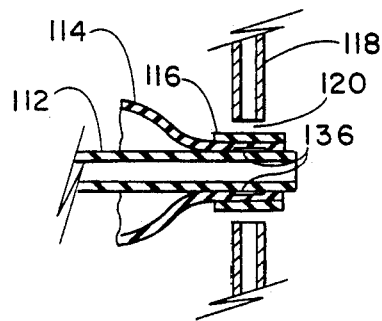
FIG. 12 is a side elevation of the distal end region of a balloon catheter and the fixture.
Figure 13:
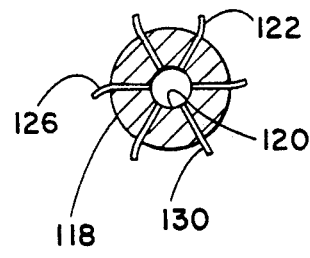
FIG. 13 is a forward sectional elevation of the fixture.
Figure 14:
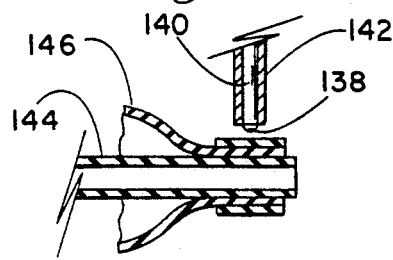
FIG. 14 is a side sectional elevation of part of an alternative embodiment fixture.

FIGS. 11-13 illustrate an alternative approach to forming the fusion bond, in which a length of catheter tubing 112, a dilatation balloon 114 and heat shrink tubing 116 are positioned within a bonding fixture 118 for directing multiple beams of laser energy onto the bond site. Fixture 118 includes a central opening 120 for receiving the tubing and balloon shaft, and further includes six radial openings for accommodating six optical fibers 122-132. The optical fibers are connected in common to a laser energy source 134. Thus, a single beam is effectively split into six identical beams, distributed uniformly about the bond area and slightly overlapping one another along the annular bond site to insure substantially even energy distribution.

Due to the use of fiber optics in this system, it is preferable to generate laser energy at a wavelength in the near infrared range, more particularly at about 1.06 microns. The near infrared wavelength, as compared to the far infrared wavelength previously discussed, is not as well matched to the absorption spectra of the polymeric materials forming the dilatation balloon and catheter tubing. Consequently, a coating of a dark ink or polymeric film is applied to the exterior of catheter tubing 112 at the bond site, and thus provides enhanced energy absorption at the interface, as is best seen at 136 in FIG. 12.

The system in FIGS. 11-13 forms satisfactory bonds without focusing optics, so long as sufficient power (less than 10 watts) is provided in laser source 134 and the optical fiber terminations are positioned sufficiently close to the dilatation balloon and tubing. If desired, however, the laser energy can be more effectively concentrated at the bond site with focusing optics, e.g. a planar-convex lens at the tip of each optical fiber near the bond site, as shown at 138 in connection with an optical fiber 140 in a fixture 142 similar to fixture 118. Lens 138 of course is selected to focus the beam at the interface between a length of catheter tubing 144 and a dilatation balloon 146 along the bond site.

One apparent advantage of the bonding approach shown in FIGS. 11-14 is the ability to maintain the fixture, beams, and polymeric components stationary as the bond is formed. A further advantage is that multiple beam fixtures can be fashioned to accommodate noncircular bonds, e.g. for catheter tubing having the cross section of an oval or ellipse in the bond region.

While only the distal bond is discussed in detail, it is to be appreciated that forming a proximal bond between the proximal shaft of the dilatation balloon and catheter tubing is substantially the same. The only significant difference is the absence of any step similar to the cutting of the distal tip to a preferred length as described in connection with FIG. 9. Proximal and distal bonds formed according to the present invention have been found to withstand substantial burst pressures, specifically in the range of about 425 pounds per square inch. In fact, under testing the dilatation balloon itself tends to burst, prior to the failure of either fusion bond, even with the axial dimension of the distal fusion bond as low as 0.020 inches. Uniformity of the bonds is enhanced by fusion with concentrated, monochromatic energy. Finally, concentration of the energy in combination with the high absorption of the selected wavelength, virtually eliminates unwanted heat conduction in axial directions away from the bond site, permitting placement of bonds adjacent to the proximal and distal cones of the dilatation balloon, without any substantial crystallization and stiffening of the cones.

The preferred embodiment balloon catheter 16 is of coaxial construction. It is to be understood that alternative catheter constructions, for example multilumen catheters, can be manufactured according to the process described above, within the scope of the present invention.

What is claimed is:

1. A balloon catheter comprising:
an elongate pliable length of catheter tubing formed of a polymeric material and having a proximal end and a distal end;
a polymeric dilatation balloon mounted to the catheter tubing near the distal end and in surrounding relation to the catheter tubing, said balloon including a medial region, proximal and distal neck regions each substantially smaller in diameter than the medial region, and proximal and distal tapered regions between the medial region and the proximal and distal neck regions, respectively, each of the tapered regions diverging in the direction from its associated neck region to the medial region, the distal neck region being contiguous with the catheter tubing to define a distal interface; and
a distal fluid tight fusion bond along the interface of the catheter tubing and the distal neck region, said fusion bond being spaced apart from the distal tapered region by a distance of at most 0.030 inches, and wherein the distal tapered region is substantially free of crystallization.

2. The balloon catheter of claim 1 wherein:
the axial dimension of the distal fusion bond is at most 0.030 inches, and the distal fusion bond is spaced apart from the distal tapered region by less than 0.010 inches.

3. The balloon catheter of claim 1 wherein:
the catheter tubing and the balloon are formed of different polymeric materials.

4. The balloon catheter of claim 3 wherein:
the catheter tubing comprises an extrusion of at least one thermoplastic polymeric material chosen from the group consisting of: polyesters, polyolefins, polyamides, thermal polyurethanes and their copolymers.

5. The balloon catheter of claim 3 wherein:
the balloon is formed of at least one of the materials from the group consisting of: polyethylene terephthalate, nylon, polyolefin and their copolymers.

6. The balloon catheter of claim 1 further including:
a fluid tight proximal fusion bond between the catheter tubing and the proximal end region, said proximal fusion bond being axially spaced apart from the proximal tapered region by at most 0.030 inches, and wherein the proximal tapered region is substantially free of crystallization.

7. A balloon catheter comprising:
an elongate pliable length of catheter tubing formed of a polymeric material and having a proximal end and a distal end;
a polymeric dilatation balloon mounted to the catheter tubing near the distal end and in surrounding relation to the catheter tubing, said balloon including a medial region, proximal and distal neck regions each substantially smaller in diameter than the medial region, and proximal and distal tapered regions between the medial region and the proximal and distal neck regions, respectively, each tapered region diverging in the direction from its associated neck region to the medial region; and
proximal and distal fluid tight fusion bonds between the catheter tubing and the proximal and distal neck regions, respectively, wherein each of the proximal and distal fusion bonds is within 0.030 inches of its associated one of the proximal and distal tapered regions, and wherein each of proximal and distal tapered regions is substantially free of crystallization.

8. The balloon catheter of claim 7 wherein:
the inner diameter of the distal neck portion is substantially equal to the outer diameter of the catheter tubing in the region of said distal fusion bond, and the inner diameter of the proximal neck region is substantially equal to the outer diameter of the catheter tubing along the proximal fusion bond.

9. The balloon catheter of claim 8 wherein:
the catheter tubing, neck regions and fusion bonds are annular.

10. The balloon catheter of claim 9 wherein:

the axial dimension of the distal fusion bond is at most 0.030 inches.

11. The balloon catheter of claim 10 wherein:
the axial length of the distal fusion bond is about 0.020 inches.

12. The balloon catheter of claim 11 wherein:
the distal fusion bond is less than 0.010 inches from the distal tapered region.

13. The balloon catheter of claim 7 wherein:
the catheter tubing comprises an extrusion of at least one thermoplastic polymeric material chosen from the group consisting of: polyesters, polyolefins, polyamides, thermoplastic polyurethanes and their copolymers.

14. The balloon catheter of claim 13 wherein:
the balloon is formed of at least one of the materials from the group consisting of: polyethylene terephthalate, nylon, polyolefin, and their copolymers.

15. The balloon catheter of claim 7, formed according to a process comprising the steps of:
positioning the polymeric dilatation balloon along and in surrounding relation to the length of catheter tubing, with the dilatation member and the catheter tubing aligned to place a first surface portion of the dilatation balloon and a second surface portion of the catheter tubing in a contiguous and confronting relation;

generating substantially monochromatic energy at a wave length selected to at least approximately match a wave length of maximum spectral absorption of the polymeric materials forming the dilatation balloon and the catheter tubing;

controllably directing the monochromatic energy onto the catheter tubing and the dilatation balloon to concentrate the monochromatic energy in a narrow bond site circumscribing the catheter tubing and running along the interface of the first and second surface portions, thus to melt the polymeric materials only along the bond site and the immediate region thereof; and allowing the previously melted polymeric materials to cool and solidify to form a fusion bond between the catheter tubing and the dilation balloon.

16. The balloon catheter of claim 15 wherein:
said interface of the first and second surfaces is annular, and the step of directing the monochromatic energy includes focusing the beam to position a focal area of the beam substantially at the interface, and moving the focal area, relative to the catheter tubing and the dilation balloon, in an annular path along the interface to define said bond site.

* * * * *

UNITED STATES PATENT AND TRADEMARK OFFICE
CERTIFICATE OF CORRECTION

PATENT NO. : 5,267,959
DATED : December 7, 1993
INVENTOR(S) : Michael R. Forman

It is certified that error appears in the above-indentified patent and that said Letters Patent is hereby corrected as shown below:

On the title page, Item [73]: Assignee change
"Schneider, Inc." to read -- Schneider (USA) Inc. --.

Column 16, line 25

Claim 16, line 7 the word "dilation" should read
-- dilatation --.

Signed and Sealed this

Fourteenth Day of June, 1994

Attest:

BRUCE LEHMAN

*Attesting Officer*      *Commissioner of Patents and Trademarks*